(12) United States Patent
Cannon et al.

(10) Patent No.: US 9,119,740 B2
(45) Date of Patent: Sep. 1, 2015

(54) INTRODUCER SHEATH

(75) Inventors: Tiffani L. Cannon, Bloomington, IN (US); Brent A. Mayle, Spencer, IN (US); James C. Merk, Terre Haute, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 235 days.

(21) Appl. No.: 13/570,734

(22) Filed: Aug. 9, 2012

(65) Prior Publication Data

US 2014/0046425 A1 Feb. 13, 2014

(51) Int. Cl.
*A61F 2/958* (2013.01)
*A61F 2/962* (2013.01)
*A61M 25/00* (2006.01)

(52) U.S. Cl.
CPC ............. *A61F 2/962* (2013.01); *A61M 25/005* (2013.01); *A61M 2025/0047* (2013.01)

(58) Field of Classification Search
CPC ............. A61F 2/958; A61M 25/0053; A61M 25/0045; A61M 25/0054; A61M 2205/3331; A61M 2025/09191; A61M 25/00; A61B 1/00071; A61B 5/6851
USPC ....... 72/135, 371; 140/71; 138/123; 600/139, 600/585; 623/1.11; 604/524, 527
See application file for complete search history.

(56) References Cited

U.S. PATENT DOCUMENTS

| | | | |
|---|---|---|---|
| 5,251,640 A | 10/1993 | Osborne | 128/772 |
| 5,380,304 A | 1/1995 | Parker | 604/282 |
| 5,702,373 A * | 12/1997 | Samson | 604/527 |
| 5,769,830 A | 6/1998 | Parker | 604/282 |
| 5,792,124 A | 8/1998 | Horrigan et al. | 604/282 |
| 6,152,912 A | 11/2000 | Jansen et al. | 604/526 |
| 6,258,080 B1 | 7/2001 | Samson | 604/525 |
| 6,824,553 B1 | 11/2004 | Samson et al. | 606/192 |
| 6,881,194 B2 * | 4/2005 | Miyata et al. | 600/585 |
| 6,939,337 B2 | 9/2005 | Parker et al. | 604/528 |
| 7,117,703 B2 * | 10/2006 | Kato et al. | 72/135 |
| 2001/0034514 A1 | 10/2001 | Parker | 604/525 |
| 2002/0072689 A1* | 6/2002 | Klint | 600/585 |
| 2003/0083730 A1* | 5/2003 | Stinson | 623/1.11 |
| 2003/0135198 A1* | 7/2003 | Berhow et al. | 604/524 |
| 2009/0254107 A1 | 10/2009 | Katoh et al. | 606/159 |
| 2010/0049168 A1* | 2/2010 | Parker et al. | 604/527 |
| 2010/0057051 A1 | 3/2010 | Howat et al. | 604/526 |

* cited by examiner

*Primary Examiner* — Katrina Stransky
*Assistant Examiner* — Sidharth Kapoor
(74) *Attorney, Agent, or Firm* — Brinks Gilson & Lione

(57) ABSTRACT

An introducer sheath has a proximal segment and distal segment. The proximal segment includes an inner portion, and a polymeric outer covering portion. The inner portion is formed from a plurality of elongated strands circularly positioned around a longitudinal axis. Each strand includes axial twist portions arranged to define a generally helical strand profile, wherein the twist portions are complementary with twist portions of adjacent strands to define the tubular segment. A tubular distal segment is dimensioned to receive an elongated stent for deployment. The length of the proximal segment is greater than the length of the distal segment, and the outer diameter of the distal segment may exceed that of the proximal segment. A stability sheath may be received over the proximal segment to enhance the stability of the sheath.

20 Claims, 5 Drawing Sheets

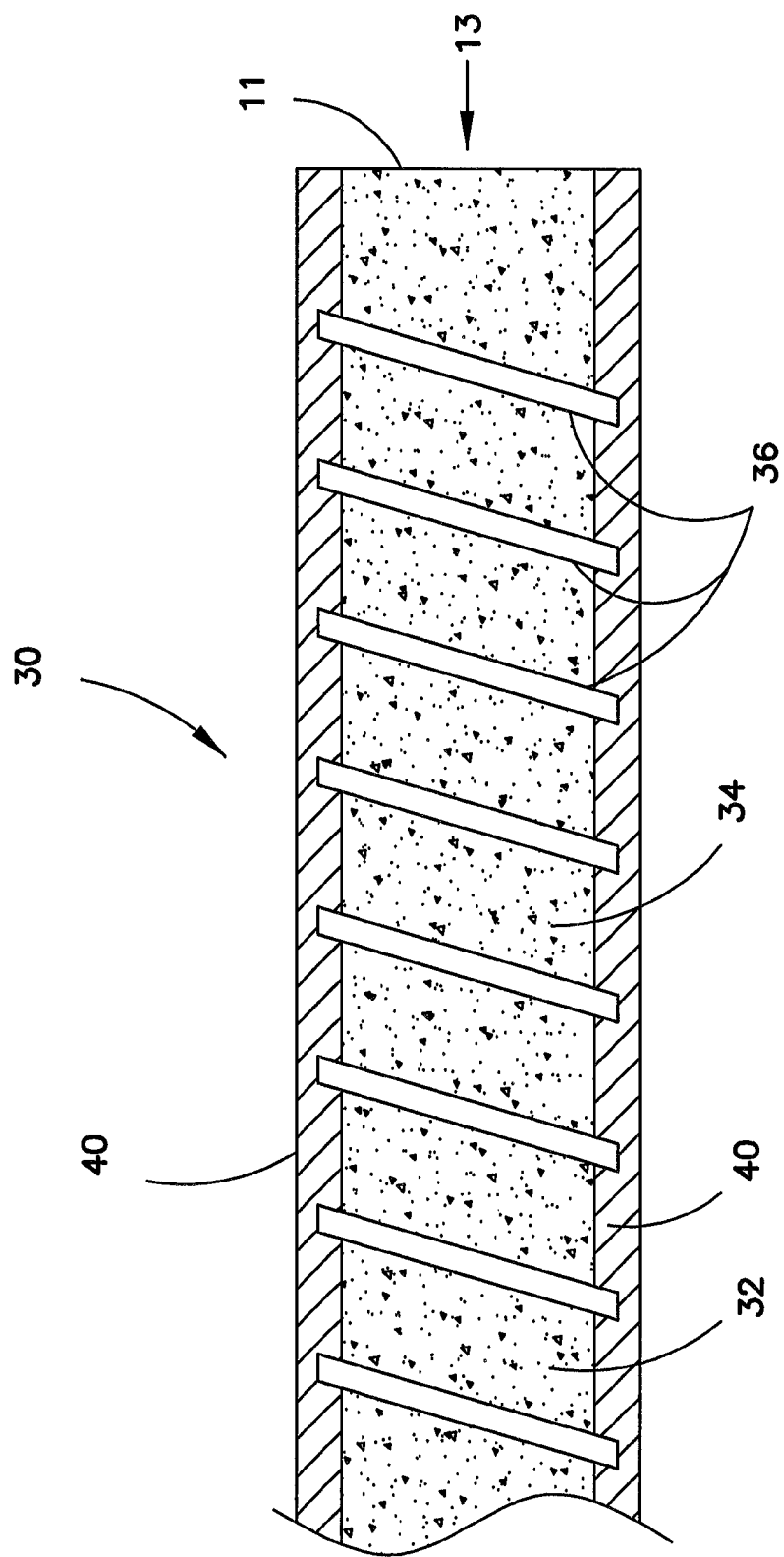

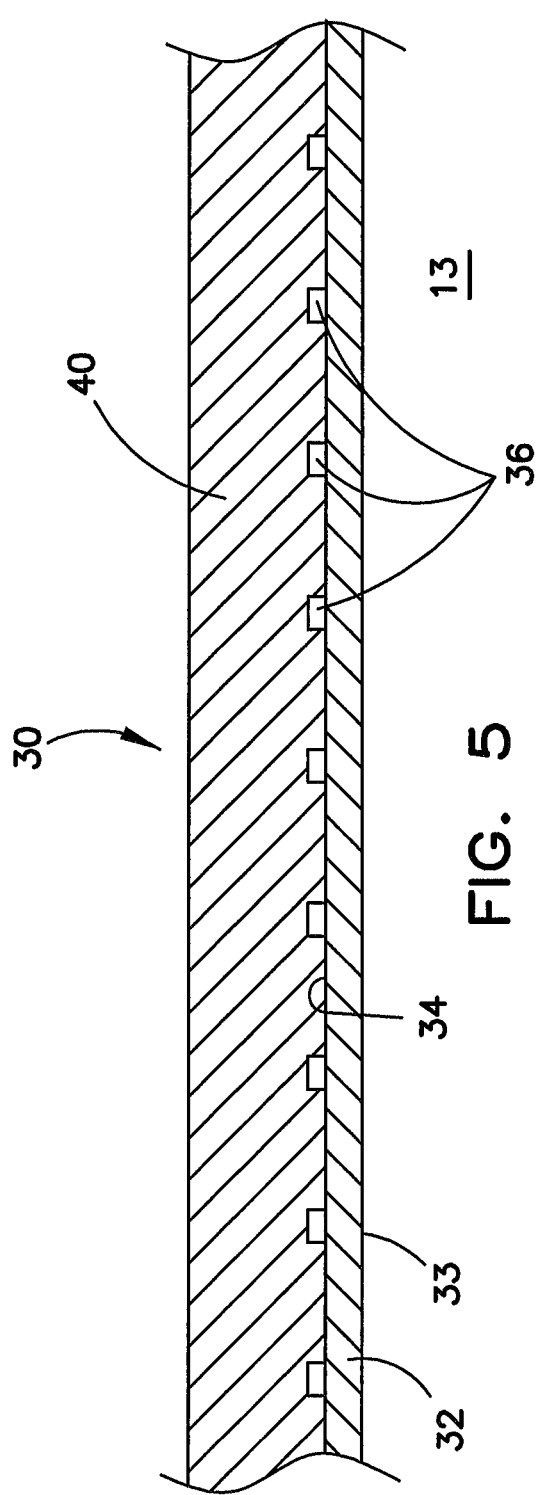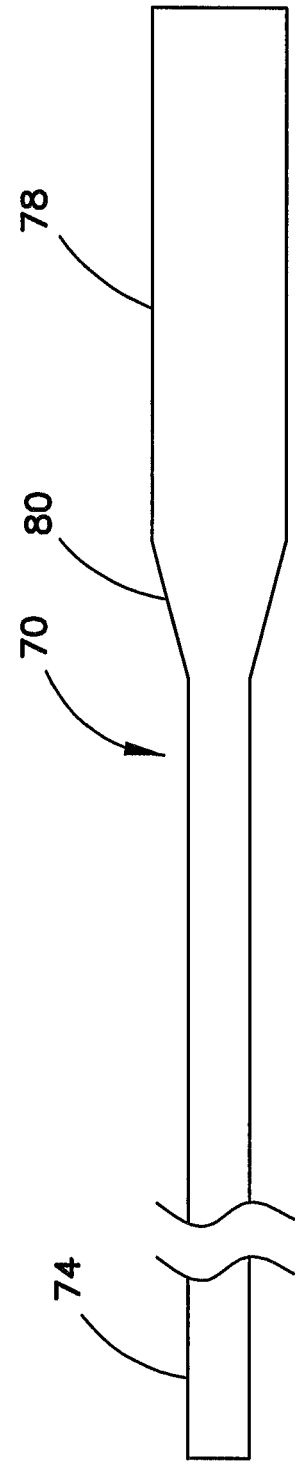

INTRODUCER SHEATH

BACKGROUND

1. Technical Field

This invention relates to the field of medical devices, and more particularly, to an introducer sheath for use in deploying an expandable medical device into a body passageway of a patient.

2. Background Information

Numerous advances of considerable note have occurred in medical surgical techniques over the last few decades. Among the most significant advances has been the adoption, and now-routine performance, of a wide variety of minimally invasive procedures. When carrying out such procedures, access to a site of concern within a patient is achieved through a relatively small incision, into which a tubular device (such as a sheath) is inserted or introduced. The sheath keeps the incision open while permitting access to the target site via the interior (i.e., lumen) of the sheath. Non-limiting examples of such devices include introducer sheaths, guide catheters, and like devices (devices collectively referred to herein as "sheaths" or "introducer sheaths").

Body passageways in which medical interventional devices, such as stents, are now commonly introduced include the esophagus, trachea, colon, biliary tract, urinary tract, and vascular system, among other locations within the body. When placing a medical interventional device in a passageway, communication with the passageway is typically attained by initially inserting the distal end of introducer sheath into the body passageway. Since the introducer sheath must often traverse tortuous pathways to reach the target site, the sheath often includes a coil reinforcement to facilitate passage through the pathways without kinking. Examples of introducer sheaths of this type are described in U.S. Pat. No. 5,380,304, and U.S. Pat. Publ. No. 2001/0034514, both incorporated by reference herein. The sheaths described in these patents include a lubricious inner liner having a helical coil fitted over the liner. An outer tube is connected to the outer surface of the liner through the coil turns. The coil reinforcement imparts kink resistance to this thin-walled sheath through a wide range of bending.

Another example of an introducer sheath is provided in U.S. Pat. No. 5,792,124, incorporated by reference herein. This patent discloses an introducer sheath having a woven braid as a reinforcing member. Although braided and coiled structures are now routinely used as reinforcements in tubular medical devices, those skilled in the art recognize that these reinforcements are not generally considered interchangeable. A coil is typically utilized in a sheath to minimize the possibility of the sheath kinking, and/or to minimize ovalization of the sheath lumen during bending of the sheath. On the other hand, a braid is typically utilized when it is desired to impart stiffness, pushability, or torqueability to the sheath.

The medical interventional device, such as an expandable stent, etc., is delivered to the target site from a lumen in the introducer sheath. Typically, the device is positioned at the target site by withdrawing the introducer sheath from around the stent while the stent is in a constricted condition. An inner catheter may be provided in the sheath lumen for preventing the stent from withdrawing with the sheath. In an alternative arrangement, the constricted stent may be pushed from the distal end of the sheath by a pusher mechanism positioned in the sheath lumen. In either technique, upon deployment at the target site, the device expands to the diameter of the surrounding body passageway.

Deployment of expandable devices, such as stents, in this manner is now a routine practice, and such deployment is often carried out with only a minimum of complications, if any. This is particularly true when the device has a relatively short length (e.g., less than about 80 mm) and/or a relatively modest outer diameter. However, as medical technology has progressed, stents and other interventional devices having longer lengths (e.g., about 100 to 300 mm or more) and/or having outer coatings, coverings, etc., that increase the effective outer diameter of the stent have become more common. When such stents are placed in a sheath lumen for delivery to the target site, the greater length and/or outer diameter of such stents increases the deployment forces necessary to extract the stent from the sheath when compared to shorter and/or lesser diameter stents. This increase in deployment forces is due primarily to the increased outward forces exerted by the longer and/or greater diameter devices on the interior wall of the sheath.

In this event, an introducer sheath having a coiled reinforcement has a tendency to stretch longitudinally as it is withdrawn from around the interventional device. Although this phenomenon may occur to a lesser degree with non-coated, non-covered, or shorter interventional devices, it is more pronounced with the coated, covered, or longer diameter devices. With such coated, covered or longer diameter devices, the stretching of the sheath causes the distance between adjacent turns of the coil to increase. This longitudinal expansion of the reinforcing coil adversely affects the ability of the sheath wall to withstand the radial expansive forces exerted on the interior of the wall by the stent, which may result in pockets being formed in the sheath wall between adjacent coil turns. When this occurs, surfaces of the undeployed stent may expand into such pockets, thereby undesirably increasing the resistance imparted by the stent upon the sheath, and hindering efficient deployment of the stent. In addition, the sheath may elongate as it is withdrawn from the stent. When such elongation occurs, the distance the sheath handle is capable of traveling upon deployment is reduced. A limited travel path for the sheath holder may present the stent from being fully deployed from the sheath into the vessel.

A sheath having a braid reinforcement is also prone to longitudinal stretching, or elongation, upon withdrawal from the stent, due to the increased deployment forces exerted on the sheath wall. With a braid reinforcement, such elongation reduces the inner diameter of the sheath to an extent that the stent cannot be efficiently extracted therefrom, if possible at all. Alternatively, such elongation may necessitate the use of a larger diameter sheath than may be desired, so that the stent can still be deployed therefrom in light of the expected elongation and reduction in diameter of the braided sheath upon use.

It is desired to provide an improved introducer sheath or other medical apparatus suitable for traversing tortuous passageways in the patient's anatomy during deployment of a medical interventional device, such as an expandable stent. More particularly, it is desired to provide an introducer sheath that is capable of minimizing elongation or stretching during withdrawal of the sheath from a medical interventional device, thereby providing for more efficient withdrawal of the sheath when used to position the interventional device in a body passageway.

SUMMARY

The shortcomings of the prior art are addressed by the present invention. In one form thereof, the invention comprises a sheath comprising a tubular proximal segment having a proximal end, a distal end, an inner portion, and a polymeric outer covering portion. The inner portion comprises a plurality of elongated strands circularly positioned around a longitudinal axis, each strand including axial twist portions arranged to define a generally helical strand profile. The twist portions are complementary with twist portions of adjacent strands along a length of the inner tubular portion for defining the tubular segment thereby. The tubular proximal segment has a first length and a first outer diameter. A tubular distal segment has a proximal end, a distal end, a second length, and a second outer diameter. The first length is greater than the second length, and the second outer diameter is greater than the first outer diameter. A tapered transition is disposed intermediate the tubular proximal and distal segments along a length of the sheath.

In another form thereof, the invention comprises an assembly comprising an introducer sheath and a medical interventional device, such as a stent, received in a passageway of the sheath. The introducer sheath comprises a tubular proximal segment and a tubular distal segment. The tubular proximal segment has a proximal end, a distal end, an inner portion and an outer covering portion. The inner portion comprises a plurality of elongated strands circularly positioned around a longitudinal axis. Each strand includes axial twist portions arranged to define a generally helical strand profile, wherein the twist portions are complementary with twist portions of adjacent strands along a length of the inner tubular portion for defining the tubular segment thereby. The tubular proximal segment has a first length and a first outer diameter. The tubular distal segment has a proximal end, a distal end, a second length, and a second outer diameter, such that the first length is greater than the second length. The medical interventional device is received in the passageway at the tubular distal segment and is deployable therefrom.

BRIEF DESCRIPTION OF THE DRAWINGS

FIG. 4 is a longitudinal view of the distal end of the sheath of FIG. 1, partially in section;

FIG. 5 is a longitudinal cross-sectional view of a portion of the wall of the distal sheath segment, taken along line 5-5 of FIG. 1;

FIG. 6 is a side view of a mandrel used for forming the sheath of FIG. 1.

DETAILED DESCRIPTION OF THE DRAWINGS AND THE PRESENTLY PREFERRED EMBODIMENTS

Figure 1:
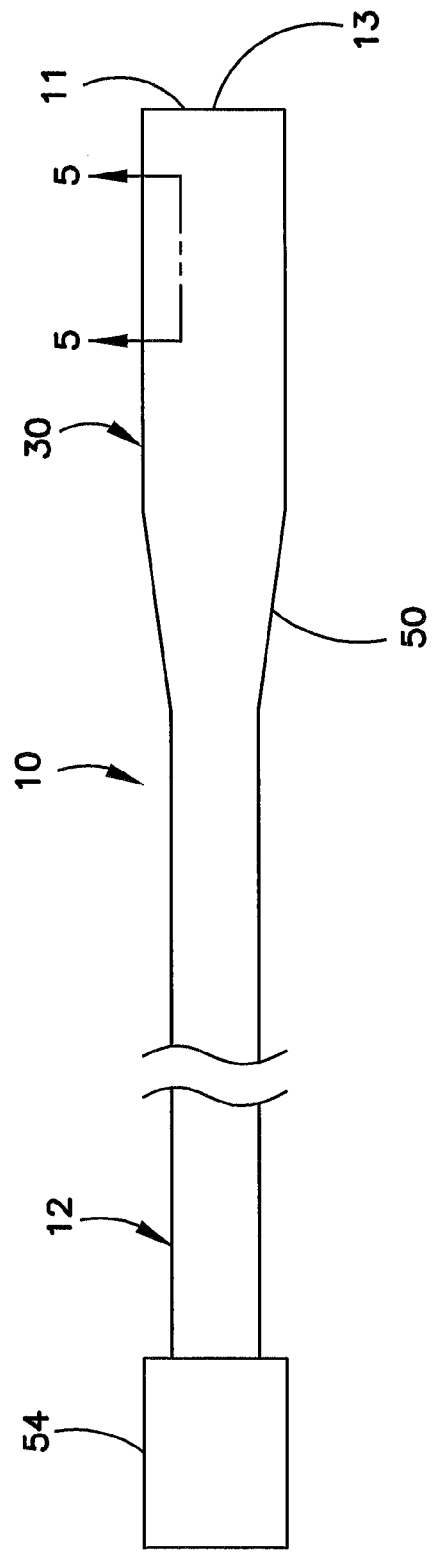
FIG. 1 is a side view of an introducer sheath according to one embodiment of the present invention.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" will be used to describe the opposing axial ends of the sheath, as well as the axial ends of various segments and component features of the sheath. The term "proximal" is used in its conventional sense to refer to the end of the sheath (or component thereof) that is closest to the operator during use of the device. The term "distal" is used in its conventional sense to refer to the end of the sheath (or component thereof) that is initially inserted into the patient, or that is closest to the patient during use.

When conventional introducer sheaths are used to deploy a medical interventional device, such as a stent, having a relatively short length, such deployments may often be carried out without undue complication. Typically, the stent is nested, or housed, in the distal portion of the sheath in a radially compressed condition. As the stent is deployed from the distal end of the sheath, the stent radially expands to the diameter of the body passageway in which it has been deployed. The relatively short length of the stent, often less than about 80 mm in length, typically provides minimal resistance to the interior of the sheath as the compressed sheath is deployed therefrom.

When comparatively longer stents (e.g., stents greater than about 100 mm in length, and particularly, stents greater than about 140 mm in length) are deployed from prior art sheaths, however, the deployment of the stent from a sheath may be less than optimal. Due to the greater length of these stents, a greater aggregate outward force is exerted by the compressed stent upon the interior wall of the sheath, when compared to the force exerted by a stent of a lesser length. As a result, a higher push force must typically be imparted by the inner catheter to overcome the tendency of the stent to remain with the sheath as the sheath is withdrawn from the passageway. A high push force as described may also be required upon deployment of coated or covered stents from the sheath. This is due to the increased forces exerted against the wall of the sheath by the larger diameter coated or covered stent when compared to an otherwise similar, but uncoated or uncovered stent.

The forces exerted by the compressed stent upon the interior wall of the sheath upon deployment may cause the sheath to stretch in the longitudinal direction as the sheath is withdrawn from around the stent. Such stretching may have little practical significance when smaller-length stents are positioned within the sheath. However, with longer stents, the increased stent length results in greater radially outwardly directed forces exerted by the constricted stent within the sheath.

This phenomenon is not exclusive to the use of longer stents, and may occur when deploying stents less than 80-100 mm in length. However, the effect is generally more pronounced with longer stents, and/or with coated or covered stents of any length wherein the additional diameter imparted to the stent by the coating/covering requires additional forces upon deployment. In some instances, such as with particularly long stents (e.g., 170-200 mm in length), and/or with highly coated or covered stents, the stent cannot be deployed at all.

FIG. 1 is a side view of an introducer sheath 10 according to one embodiment of the present invention. Sheath 10 includes two tubular sub-assemblies, or segments, namely proximal segment 12 and distal segment 30. A passageway 13 extends axially through sheath 10. In the example shown, segments 12 and 30 are axially bonded along a tapered transition 50. The proximal end of proximal segment 12 is receivable in a base structure, such as the handle 54 shown schematically in FIG. 1. Those skilled in the art will appreciate that various other conventional proximal attachments, such as a hub, a manifold, a guide catheter, etc., may alternatively receive the proximal end of proximal sheath segment 12.

Figure 2:
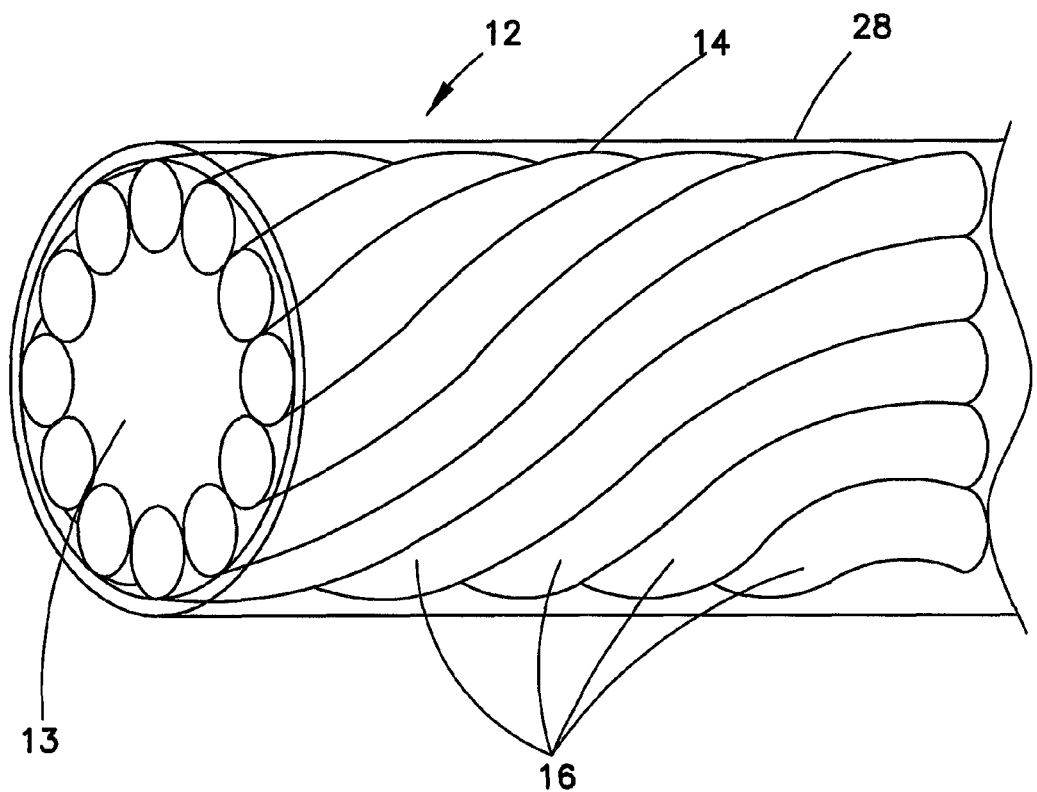
FIG. 2 is an enlarged longitudinal view of a portion of the proximal segment of the sheath of FIG. 1.

FIG. 2 is an enlarged view of the proximal end portion of proximal segment 12. Proximal segment 12 comprises an inner tubular structure 14 and an outer jacket 28 covering the inner tubular structure. In the version shown in the figure, outer jacket 28 is transparent. In other variations outer jacket 28 is not transparent, or is partially transparent.

Figure 3:
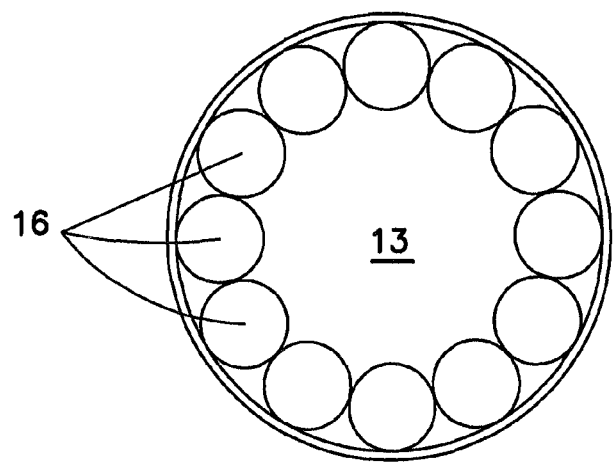
FIG. 3 is an end view of the proximal end of the sheath.

Inner tubular structure 14 is formed from a plurality of elongated strands 16. As shown, strands 16 are circularly positioned around a longitudinal axis extending through sheath 10. Each strand 16 is twisted as shown in FIG. 2 to define a generally helical strand profile. Each of the strand twist portions is complementary with the twist portions of adjacent strands along the length of inner tubular structure 14 to define the hollow tubular structure as shown. FIG. 3 is a view taken from the proximal end of segment 12.

Those skilled in the art will recognize that the twisting of strands 16 is similar to the twist conventionally applied to wire rope or cable. Like conventional wire rope, strands 16 may be twisted by use of a conventional wire, or rope, twist machine. Unlike most ropes or cables, however, the interior of proximal segment 12 is hollow. When a conventional rope twist machine is utilized, adjacent strands 16 may be subjected to compression forces when twisted so that they securely engage each other without the formation of gaps therebetween. Alternatively, or in addition to, such compression forces, the strands can undergo other treatments to achieve, and maintain, secure engagement therebetween, such as the application of a biocompatible adhesive to the strands.

Strands 16 may be formed of conventional metals, metal alloys, composite materials, polymers, etc., as are conventionally used in the medical arts. In one non-limiting example, the strands are formed from stainless steel, such as SUS 304, SUS 316, etc. In another example, the strands may be formed from nitinol, a nickel-titanium alloy. Strands 16 need not all be formed of the same composition, and need not necessarily have the same dimensions. The strands are preferably treated in any known manner to remove or reduce residual stress in the strands, such as via heat treatment. In addition, each strand 16 need not necessarily comprise a single unit as shown in these figures. In this alternative, each strand 16 can comprise a bundle of individual strand units arranged to functionally comprise a strand.

As stated, inner tubular structure 14 is covered with an outer jacket 28. Preferably, outer jacket 28 comprises a synthetic resin such as a fluorocarbon (e.g., PTFE), a polyamide (nylon), a polyurethane, a polyether block amide, and the like. Jacket 28 may be applied to the outer surface of tubular structure 14 by any conventional manner, such as by heat shrinking the jacket over the tubular structure in a conventional heat shrink oven. Heat shrinking a polymeric jacket onto a tubular member is well known in the medical arts, and is further described, e.g., in the incorporated by reference U.S. Pat. No. 5,380,304, and U.S. Pat. Publ. No. 2001/0034514, cited above. Those skilled in the art will appreciate that the outer diameter of proximal segment 12 may be varied depending upon the intended use of the sheath. In one example, the proximal segment may have an outer diameter between about 1.67 and 2.0 mm (5 and 6 French), and more particularly, between about 1.78 and 1.83 mm.

During formation of sheath proximal segment 12, outer jacket 28 may extend approximately 1-2 cm distal of the distal end of inner tubular structure 14. As further described herein, this additional jacket material may be provided for bonding to a similar length of material extending proximal of the proximal end of distal segment 30. If desired, outer jacket 28 may also extend a short distance (e.g., about 1-2 cm) proximal of tubular structure 14.

Additional details not discussed herein for forming proximal segment 12 are provided, for example, in U.S. Pat. No. 6,881,194 and U.S. Pat. No. 7,117,703, both incorporated by reference herein. The '194 and '703 patents provide examples that describe the formation of tubular materials formed of twisted, helical strands. Other details of construction not specifically mentioned herein are believed to be well within the ability of one of ordinary skill in the art. Tubular members suitable for use herein in proximal segment 12 are commercially available, e.g., from Asahi Intecc, as ACTONE® cable tube, and from Fort Wayne Metals as HHS® tube.

Distal segment 30 is illustrated in FIGS. 4 and 5. FIG. 4 is a longitudinal view, partially in section, of a portion of distal segment 30. FIG. 5 is a longitudinal cross-sectional view of a portion of the wall of distal segment 30, taken along line 5-5 of FIG. 1. As illustrated in this example, distal segment 30 comprises a layered structure having an inner liner 32, a reinforcing member 36 positioned over the inner liner, and an outer jacket 40 that envelopes the inner liner and reinforcing member.

The inner liner 32 of the distal segment is preferably formed of a lubricious material. The lubricious material may comprise a fluoropolymer, such as PTFE or FEP. Lubricious inner liners for sheaths are well known in the medical arts, and those skilled in the art can readily select an appropriate liner for a particular use. The lubricious material provides a slippery, low friction inner surface 33 to ease deployment of a medical interventional device, such as a stent. Liner 32 preferably has a substantially uniform inner diameter that extends the entire length of distal segment 30. This allows deployment from the sheath of an interventional device having the largest possible diameter. The radially outer surface 34 of liner 32 may be roughened in any conventional manner, such as by machine grinding or chemical etching, to form an irregular surface. Providing an irregular outer surface facilitates bonding of the liner with the inner surface of outer jacket 40. The wall of the inner liner 32 should have sufficient radial rigidity to prevent the turns of the reinforcing member 36 from protruding into the longitudinal passageway extending through distal segment 30.

Inner liner 32 will typically have a uniform inside diameter between about 1 mm (3 Fr) and about 8 mm (24 Fr). One exemplary diameter is about 3.3 mm (10 Fr). The wall thickness of inner liner 20 will typically range between about 0.0254 mm and 0.76 mm (0.001 and 0.003 inch), and is preferably about 0.038 mm (0.0015 inch). Even larger, or smaller, inside diameters and/or wall thicknesses may be appropriate in a particular case. Those skilled in the art will appreciate that all dimensions recited herein are exemplary only, and that the device may be constructed to be of any size necessary as appropriate to accomplish the purposes for which the sheath is to be employed.

In the example shown in FIGS. 4 and 5, reinforcing member 36 comprises a helical coil. The coil may be formed from materials well known for such use in the medical arts, such as a metal, a metal alloy (e.g., stainless steel or a shape memory composition such as nitinol), a multi-filar material, a composite material, etc. In order to minimize the outer diameter of the distal segment 30, it is preferred to provide a coil with a conventional flat wire construction. However, those skilled in the art will appreciate that coil materials of other cross-sectional configurations, such as round, oval, and various other geometric configurations, may be substituted if desired. Coil 36 may extend substantially the entire length of distal segment. Preferably, however, the coil stops short of the proximal and distal ends of the distal segment. As shown in FIG. 4, terminating the reinforcing member short of the distal end 11 facilitates the ability to form a desired configuration (e.g., a distal taper) at the non-reinforced distal end, if desired. Terminating short of the proximal end facilitates joinder with proximal segment 12, as further described herein.

Although reinforcing member 36 comprises a coil in the embodiment shown, other reinforcing member configurations known in the art, such as a woven braid, may be substituted. As another alternative, a reinforcing member comprising a combination of a coil and a braid can be substituted. As a still further alternative, not all embodiments require the presence of a reinforcing member. In such embodiments, the reinforcing member may be omitted.

Outer jacket 40 may comprise a polymeric material capable of forming a secure bond with inner liner 32, and more preferably, with a roughened outer surface 34 of the liner. Preferably, outer jacket 40 comprises a heat formable polymeric material, such as a polyether block amide, a polyamide (nylon), a polyurethane, and the like. The heat formable material melts upon heating, such that portions of the material flow between the respective turns of the coil, and bond to the roughened outer surface 34 of the inner liner. Other outer layer compositions that are capable of securely bonding, adhering, or otherwise securely engaging the inner liner may be substituted. During formation of sheath distal segment 30, outer jacket 40 may extend approximately 1-2 cm proximal of the proximal end of reinforcing member 36. As further described herein, this additional jacket material may be provided for bonding to the length of material extending distal of the distal end of proximal segment 12. In one example, distal segment 30 may have an outer diameter of between about 1.8 and 2.3 mm, and more particularly, between about 1.98 and 2.10 mm.

One method of forming the distal sheath segment 30 will now be described. Initially, the inner liner 32 is placed on a suitably-sized mandrel. Generally, the mandrel will have an outer diameter substantially the same as the inner diameter of the inner liner to insure a close tolerance between the two. The coil is then positioned over the inner liner and mandrel, and the tubular outer jacket is positioned over the mandrel, liner and coil. The entire assembly is placed in a suitable heat shrink enclosure of a type well known in the art. Fluorinated ethylene propylene (FEP) is a particularly preferred composition for use herein. Those skilled in the art will appreciate that various alternative compositions for the heat shrink envelope are also suitable for use in forming this segment of the sheath, as long as the melt temperature of the material used for the outer jacket is lower than the melt temperature of the heat shrink enclosure. The heat shrink enclosure and contents are placed in an oven and baked (typically at about 385° F. (196° C.) when FEP is used as the heat shrink and a polyether block amide is used as an outer jacket material) for a suitable period of time to melt the outer jacket material so that it flows between the coil turns as described. After removal from the oven, the entire assembly is cooled, the FEP envelope is cut away, and the mandrel is removed.

Additional details of the construction or composition of the various elements of distal sheath segment 30 not otherwise disclosed are not believed to be critical to the present invention, so long as the recited elements possess the strength or mechanical properties needed for them to perform as required. Many such details not described herein are recited in detail in the incorporated-by-reference U.S. Pat. No. 5,380, 304, and U.S. Patent Publication No. 2001/0034514. Tubular members suitable for use herein as distal segment 30 are commercially available from Cook Medical Technologies LLC, as FLEXOR® sheaths.

Those skilled in the art will recognize that other inner liner, reinforcing members, and outer jacket compositions for the distal segment of the sheath may be substituted. As a further alternative, distal segment 30 need not always comprise a layered structure as described, and/or need not always include a reinforcing member. For example, a single composition structure may be substituted for the distal segment structure described hereinabove. Single composition sheath segments such as a polyimide, polyetheretherketone (PEEK), a polyamide (nylon), polytetrafluoroethylene (PTFE), fluorinated ethylene propylene (FEP), polyethylene terephthalate (PET), and the like are examples of distal sheath compositions that may be suitable for a particular application.

Proximal segment 12 and distal segment 30 may be joined to form sheath 10 according to methods known in the art. In one example a mandrel may be ground or otherwise formed to have outer dimensions that correspond to the desired inner dimensions of sheath 10. One example of a shaped mandrel 70 is shown in FIG. 6. As stated, the outer surface of mandrel 70 may be ground to comprise a smaller diameter proximal portion 74, a larger diameter distal portion 78, and a tapered portion 80 therebetween. Generally, the mandrel portion will be formed to have an outer diameter substantially the same as the inner diameter of the sheath segment received therein to insure a close tolerance between the two.

Proximal segment 12 may be slid on proximal mandrel portion 74, such that the extended distal portion of outer jacket 28 as described above extends along tapered mandrel portion 80. Distal segment 30 may be slid on distal mandrel portion 78, such that the extended proximal portion of outer jacket 40 overlaps, or underlaps, the extended outer jacket portion 28 along tapered mandrel portion 80.

Once the respective proximal and distal segments 12, 30 are arranged along the length of mandrel 70 as described, the respective extended portions of outer jackets 28, 40 are initially bonded together. One way of accomplishing such bonding is to place the proximal and distal segments in a heat shrink enclosure, such as the FEP enclosure described above, and bake this assembly in an oven at a sufficient temperature and for a sufficient time such that the respective outer jacket segments 28, 40 are bonded together at the respective extended portions. Once the segments have been bonded, the heat shrink enclosure may be skived from the assembly, and the mandrel may be removed. As an alternative to use of the heat shrink enclosure, other conventional modes of heat bonding may be substituted, e.g., bonding by use of a hot air gun.

Those skilled in the art will appreciate that proximal segment 12 and distal segment 30 need not necessarily be joined in the manner described above, and that other methods of joinder may be substituted. For example, it is not necessary that both segments 12, 30 have an extended portion. Rather, an extended portion of one of the outer jackets may extend over and be joined (e.g., via heat bonding) to the other segment. As another alternative, a discrete shaped (e.g., tapered) segment can be positioned intermediate the segments 12, along the mandrel. This intermediate segment may be bonded to the adjoining segments in any known manner. The tapered intermediate segment can comprise a material as utilized in outer jackets 28, 40, or another material that is capable of bonding thereto.

Introducer sheath 10 may be formed to have any length required to fulfill its intended purposes. In most cases, the sheath will have a length between about 40 and 200 cm. Typically, the sheath length will be between about 100 and 200 cm, such as about 125 cm. The proximal segment will generally have the greater length, and in most cases a much greater length, than the distal segment, since the distal segment need only have sufficient length to house the interventional device prior to deployment. For example, the proximal segment may be between 40 and 120 cm, and the distal segment may be between 10 and 25 cm.

Figure 7:
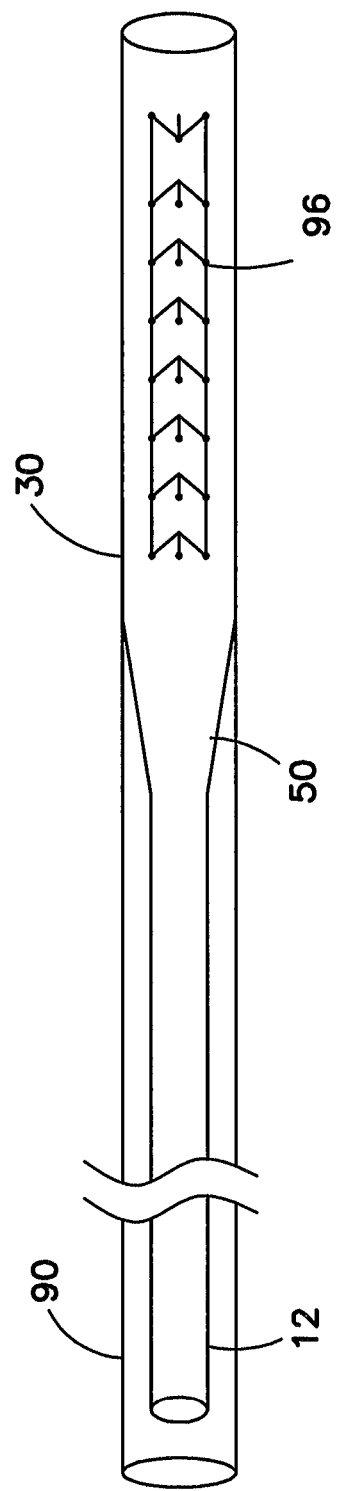
FIG. 7 is a side view of the introducer sheath of FIG. 1 illustrating a stability sheath positioned over the proximal segment of the sheath, and medical interventional device positioned within the distal passageway of the sheath.

A variation of introducer sheath 10 is shown in FIG. 7. In this variation, a stability sheath 90 is received over proximal segment 12. To provide perspective, FIG. 7 also schematically illustrates a position of a medical interventional device, such as stent 96. Stent 96 is disposed along the passageway extending interiorly of distal segment 30, and does not extend into tapered segment 50. Those skilled in the art recognize that stent 96 will typically not be visible within distal segment 30 prior to deployment.

When present, stability sheath 90 may comprise an inner liner and an outer jacket bonded to the outer surface of the inner liner. If desired, a reinforcing member, such as a coil or a braid, may be sandwiched between the inner liner and the outer jacket, in the manner described above for distal segment 30. The stability sheath 90 has a passageway extending therethrough that is dimensioned to receive proximal sheath segment 12. One example of a suitable stability sheath is the FLEXOR® sheath described above, however those skilled in the art will appreciate that other known sheath structures may be substituted. For example, the stability sheath may comprise any of the single composition sheath structures described above.

Typically, the outer diameter of the stability sheath is substantially the same as the outer diameter of distal segment 30. In this way, a smooth outer surface is provided along stability sheath 90 and sheath distal segment 30, as shown in FIG. 7. When present, stability sheath 90 reduces, or removes, slack in proximal segment 12, thereby keeping the sheath system taut as it is introduced into the vessel. In addition, the use of a stability sheath can improve deployment accuracy.

As a still further alternative, the respective proximal and distal segments 12, 30 of sheath 10 need not necessarily have differing outer diameters as shown in FIG. 1. Rather, the proximal and distal segments may be provided with a substantially similar outer diameter. In this event, the sheath will not include a tapered segment 50, nor would a stability sheath 90 be used. The proximal and distal segments can be placed in abutting relationship, and bonded or otherwise engaged in any conventional fashion. As yet another alternative, one or more intermediate segments can be positioned between proximal and distal segments 12, 30. Such intermediate segments can be provided to facilitate bonding between the proximal and distal segments, and/or to minimize transitions (e.g., flexibility differences) that may be present between the respective segments.

Deployment of various medical devices from introducer sheaths and like devices to a target site in the body is now well-known in the medical arts. Thus, further identification of a medical device suitable for deployment from sheath 10 is not required for an understanding of the invention. Non-limiting examples of medical devices that may be deployed from sheath 10 include the family of ZILVER® stents, such as the ZILVER® PTX stents, available from Cook Medical Technologies LLC of Bloomington, Ind.

The dimensions and/or compositions of the various elements of introducer sheath 10 not specifically set forth herein should be selected in view of the proposed use of the sheath. It is believed that the selection of such features will lie within the level of skill in the art, once benefit of the present disclosure is had. While a modest amount of trial-and-error may be needed to obtain optimal dimensions, it is believed that any required experimentation will not be undue. Other details of construction or composition of the various elements not otherwise disclosed are believed to be well within the ability of one of ordinary skill in the art.

It is therefore intended that the foregoing detailed description be regarded as illustrative rather than limiting, and that it be understood that it is the following claims, including all equivalents, that are intended to define the spirit and scope of this invention.

The invention claimed is:

1. An assembly comprising:
an introducer sheath having a passageway extending longitudinally therethrough, said introducer sheath comprising a tubular proximal segment and a tubular distal segment;
said tubular proximal segment having a proximal end and extending to a distal end, an inner portion and an outer covering portion, said inner portion comprising a plurality of elongated strands extending from the proximal end and terminating at the distal end and being circularly positioned around a longitudinal axis, each strand including axial twist portions arranged to define a generally helical strand profile, said twist portions complementary with twist portions of adjacent strands along a length of said inner tubular portion for defining said tubular segment thereby without formation of gaps between said strands, said tubular proximal segment having a first length, and a first outer diameter;
said tubular distal segment having a proximal end and extending to a distal end, a second length, and a second outer diameter, said first length being greater than said second length, said tubular distal segment comprising a lubricious inner liner and a polymer outer jacket bonded to said lubricious inner liner, said lubricious inner liner extending within said tubular distal segment but not extending into the tubular proximal segment; and
a medical interventional device received in said passageway at said tubular distal segment, and deployable from said distal end thereof, said lubricious inner liner providing a slippery, low friction inner surface to thereby ease deployment of said medical interventional device;
wherein said medical interventional device comprises an expandable stent, said stent received in said passageway along said tubular distal segment in a compressed condition, and expandable to an expanded condition upon deployment from said distal end.

2. The assembly of claim 1, wherein said stent has a length of at least 140 mm.

3. The assembly of claim 1, wherein said tubular distal segment comprises a reinforcing element positioned around said inner liner, and between said inner liner and an outer jacket.

4. The assembly of claim 3, wherein said second outer diameter is greater than said first outer diameter, further comprising a tapered transition intermediate said tubular proximal and distal segments along a length of said sheath, a proximal end of said transition engaged with said distal end of the tubular proximal segment, and a distal end of said transition engaged with said proximal end of the tubular distal segment.

5. The assembly of claim 4, further comprising a stability sheath received over said tubular proximal segment.

6. The assembly of claim 5, wherein said stability sheath has an outer diameter substantially the same as the outer diameter of the tubular distal segment.

7. The assembly of claim 4, wherein said outer covering portion, said tapered transition, and said outer jacket are formed from a heat formable polymeric material.

8. The assembly of claim 7, wherein the proximal segment has a length between about 40 and 120 cm, and the distal segment has a length between about 10 and 25 cm.

9. The assembly of claim 8, wherein said stent has a length not exceeding the length of said distal segment.

10. The assembly of claim 1, wherein said proximal segment outer covering comprises a fluorocarbon, a polyurethane, a polyamide, or a polyether block amide.

11. The assembly of claim 1, wherein said strands comprise a metal, a metal alloy, a composite material, or a polymer.

12. The assembly of claim 11, wherein the strands comprise stainless steel or nitinol.

13. The assembly of claim 4, wherein said reinforcement element is a metal coil.

14. The assembly of claim 1, wherein said inner liner comprises a fluoropolymer.

15. The assembly of claim 14, wherein said outer jacket comprises a heat formable polymeric material.

16. The assembly of claim 15, wherein said stent has a length not exceeding the length of said distal segment.

17. The assembly of claim 16, wherein said strands comprise stainless steel or nitinol.

18. The assembly of claim 17, wherein said stend has a length of at least 140 mm.

19. The assembly of claim 18, wherein said second outer diameter is greater than said first outer diameter, further comprising a tapered transition intermediate said tubular proximal and distal segments along a length of said sheath, a proximal end of said transition engaged with said distal end of the tubular proximal segment, and a distal end of said transition engaged with said proximal end of the tubular distal segment.

20. The assembly of claim 19, further comprising a stability sheath received over said tubular proximal segment, wherein said stability sheath has an outer diameter substantially the same as the outer diameter of the tubular distal segment.

* * * * *

UNITED STATES PATENT AND TRADEMARK OFFICE
CERTIFICATE OF CORRECTION

PATENT NO.         : 9,119,740 B2                                  Page 1 of 1
APPLICATION NO.    : 13/570734
DATED              : September 1, 2015
INVENTOR(S)        : Cannon et al.

It is certified that error appears in the above-identified patent and that said Letters Patent is hereby corrected as shown below:

In the Claims

In column 12, claim 18, line 7, after "wherein said" replace "stend" with --stent--.

Signed and Sealed this
Third Day of May, 2016

Michelle K. Lee
*Director of the United States Patent and Trademark Office*